(12) United States Patent
Goldman et al.

(10) Patent No.: US 8,841,500 B2
(45) Date of Patent: Sep. 23, 2014

(54) PREPARATION OF ALKYL AROMATIC COMPOUNDS

(75) Inventors: Alan Stuart Goldman, Highland, NJ (US); Long Van Dinh, Marietta, GA (US); William L. Schinski, San Ramon, CA (US)

(73) Assignees: Chevron U.S.A. Inc., San Ramon, CA (US); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/612,599

(22) Filed: Sep. 12, 2012

(65) Prior Publication Data

US 2013/0116492 A1 May 9, 2013

Related U.S. Application Data

(60) Provisional application No. 61/557,230, filed on Nov. 8, 2011.

(51) Int. Cl.
- *C07C 2/66* (2006.01)
- *C07C 5/31* (2006.01)
- *C07C 5/333* (2006.01)

(52) U.S. Cl.
CPC .............. *C07C 2/66* (2013.01); *C07C 2529/70* (2013.01); *C07C 2531/22* (2013.01); *C07C 5/31* (2013.01); *C07C 5/333* (2013.01); *C07C 2531/24* (2013.01)
USPC ........... 585/457; 585/446; 585/455; 585/466; 585/467; 585/468

(58) Field of Classification Search
USPC .......... 585/319, 323, 435, 438, 440, 446, 466
See application file for complete search history.

(56) References Cited

U.S. PATENT DOCUMENTS

| | | | | |
|---|---|---|---|---|
| 5,476,980 A | * | 12/1995 | Oroskar | 585/654 |
| 5,723,710 A | * | 3/1998 | Gajda et al. | 585/467 |
| 5,780,701 A | * | 7/1998 | Kaska et al. | 585/654 |
| 6,392,109 B1 | * | 5/2002 | O'Rear et al. | 585/323 |
| 2004/0181104 A1 | * | 9/2004 | Yeh et al. | 585/444 |
| 2004/0242945 A1 | | 12/2004 | Pelati et al. | |
| 2010/0236984 A1 | | 9/2010 | Brookhardt et al. | |

OTHER PUBLICATIONS

David Morales-Morales, "Pincer Complexes. Applications in Catalysis," Dec. 7, 2004, Revista de la Sociedad Quimica de Mexico, vol. 48 No. 004, pp. 338-346.*
Morales-Morales, David, "Pincer Complexes. Applications in Catalysts" *Catalysis, Rev. Soc. Quim Mx* (2004) 48:338-346; Abstract; p. 341, col. 1 to p. 342, col. 2; p. 344, col. 2.
International Search Report from PCT/US2012/55243 mailed Nov. 19, 2012, 2 pages.

* cited by examiner

*Primary Examiner* — Thuan D Dang
*Assistant Examiner* — Candace R Chouinard
(74) *Attorney, Agent, or Firm* — E. Joseph Gess; Richard J. Schulte; Melissa M. Hayworth

(57) ABSTRACT

Provided is a process for preparing alkyl aromatic compounds. The process comprises contacting an alkane under dehydrogenation conditions in the presence of a dehydrogenation catalyst, e.g., a pincer iridium catalyst, to form olefins, and then contacting the olefins generated with an aromatic compound under alkylation conditions. Both reactions are conducted in a single reactor, and occur simultaneously.

11 Claims, No Drawings

PREPARATION OF ALKYL AROMATIC COMPOUNDS

CROSS-REFERENCE TO RELATED APPLICATIONS

This application claims benefit of U.S. Provisional Application No. 61/557,230 filed Nov. 8, 2011, entitled "Preparation of Alkyl Aromatic Compounds", the contents of which are incorporated herein by reference in their entirety.

BACKGROUND OF THE INVENTION

1. Field of the Invention

Provided is a process for preparing alkyl aromatic compounds in a single reactor More specifically, an integrated process in a single reactor using a dual catalyst system is provided where alkanes are first dehydrogenated to create olefins, and then the olefins react with arene molecules.

2. Description of the Related Art

Alkyl aromatics are organic compounds comprised of an alkyl radical attached to an aromatic ring such as benzene. Alkyl-substituted aromatic compounds currently are prepared via a two-step process requiring separate streams of olefins and aromatics.

Given the large scale application of alkyl-aromatic derived detergents or surfactants, a number of routes have been developed to produce alkylbenzenes.

The HF/n-paraffins process involves dehydrogenation of n-paraffins to olefins, and subsequent reaction with benzene using hydrogen fluoride as the catalyst. This process accounts for the majority of the installed linear alkyl aromatic production in the world. It includes a stage where n-paraffins are converted to mono-olefins (typically internal mono-olefins), a unit whose primary function is to convert residual diolefins to mono-olefins, a unit which is essentially an aromatic removal unit—introduced before the alkylation step to improve yield and quality, and an alkylation step where mono-olefins, both internal and alpha olefins, are reacted with benzene to produce alkyl aromatics in the presence of an HF catalyst.

Another process involves dehydrogenation of n-paraffins to olefins, and subsequent reaction with benzene using a fixed bed catalyst. This is newer technology and has several of the stages depicted in the HF/n-paraffins process, but it is principally different in the benzene alkylation step, during which a solid-state catalyst is employed.

A Friedel-Crafts alkylation process involves chlorination of n-paraffins to monochloroparaffins followed by alkylation of benzene using aluminum chloride ($AlCl_3$) catalyst. This method is one of the oldest commercial routes to alkyl aromatics.

Iridium complexes as catalysts are known. During the 1980s, it was discovered that certain iridium complexes are capable of catalytically dehydrogenating alkanes to alkenes under exceptionally mild thermal (i.e., less than 160° C.) or even photolytic conditions (see, e.g., *J. Am. Chem. Soc.* 104 (1982) 107; 109 (1987) 8025; *J. Chem. Soc., Chem. Commun.* (1985) 1829). For a more recent example, see *Organometallics* 15 (1996) 1532.

Pincer ligand complexes of rhodium and iridium as catalysts for the dehydrogenation of alkanes are receiving widespread attention. See, for example, F. Liu, E. Pak, B. Singh, C. M. Jensen and A. S. Goldman, "Dehydrogenation of n-Alkanes Catalyzed by Iridium "Pincer" Complexes: Regioselective Formation of α-olefins," *J. Am. Chem. Soc.* 1999, 121, 4086-4087; F. Liu and A. S. Goldman, "Efficient thermochemical alkane dehydrogenation and isomerization catalyzed by an iridium pincer complex," *Chem. Comm.* 1999, 655-656; and C. M. Jensen, "Iridium PCP pincer complexes: highly active and robust catalysts for novel homogenous aliphatic dehydrogenations," *Chem. Comm.* 1999, 2443-2449. The use of compounds such as $(PCP)MH_2$ ($PCP=C_6H_3$ $(CH_2PBut_2)_2$-2,6) (M=Rh, Ir) (1a, 1b) dehydrogenate various cycloalkanes to cycloalkenes at 200° C. with turnovers of 70-80 turnovers/hour. The reaction proceeds at 200° C. in neat solvent and without the use of a sacrificial hydrogen acceptor such as tert-butyl ethylene.

In addition, "pincer" complexes of platinum-group metals have been known since the late 1970s (see, e.g., *J. Chem. Soc., Dalton Trans.* (1976) 1020). Pincer complexes have a metal center and a pincer skeleton. The pincer skeleton is a tridentate ligand that generally coordinates with meridionial geometry. The use of pincer complexes in organic synthesis, including their use as low-temperature alkane dehydrogenation catalysts, was exploited during the 1990s and is the subject of two review articles (see *Angew. Chem. Int. Ed.* 40 (2001) 3751 and *Tetrahedron* 59 (2003)). See also U.S. Pat. No. 5,780,701. Jensen et al. (*Chem. Commun.* 1997 461) used iridium pincer complexes to dehydrogenate ethylbenzene to styrene at 150 to 200° C. Recently, pincer complexes have been developed that dehydrogenate hydrocarbons at even lower temperatures. For some recent examples, see *J. Mol. Catal. A* 189 (2002) 95, 111 and *Chem. Commun.* (1999) 2443.

Improvements in the selectivity and efficiency of preparing alkyl aromatics would be of great value to the industry. Limiting the number of steps needed would greatly enhance the efficiency of the process.

SUMMARY OF THE INVENTION

Provided is a process for preparing alkyl aromatics from an alkane. The process comprises combining an alkane, arene compound, and a dual catalyst system in a single reactor. The reactions which occur comprise contacting an alkane under dehydrogenation conditions in the presence of a dehydrogenation catalyst, e.g., an iridium catalyst complex to form olefins. The olefins then react with the arene compound under aromatic alkylation conditions with a suitable alkylation catalyst. The two steps are conducted in a single reactor, using a dual catalyst system. Conducting all steps of the process in a single reactor using a dual catalyst system greatly enhances the efficiency of the process.

In one embodiment, an iridium complex is used for dehydrogenation of the formula $LMX(X')_n$, where n=0, 1 or 2, X and X' are moieties into which a monomer can insert or which can be eliminated from the metal center to generate a catalytically active LM fragment, M is iridium, and L is a benzimidazolyl-containing ligand.

In one embodiment, the catalyst for aromatic alkylation is a zeolite catalyst, e.g., an alumina-silicate.

The present process conducts both the dehydrogenation of the alkane to the olefin, and the aromatic alkylation in a single reactor using a dual catalyst system. It has been found running both reactions concurrently in a single reactor permits one to realize great process efficiencies, and that the catalysts are compatible.

Among other factors, it has been discovered that by using a dehydrogenation catalyst, and in particular an iridium catalyst complex, with an aromatic alkylation catalyst, e.g., a zeolite, as a dual catalyst system, an efficient, integrated process for preparing alkyl aromatic compounds is achieved. In the same reactor, the two reactions of dehydrogenation and aromatic alkylation will begin to occur simultaneously. The aromatic alkylation reaction will actually help drive the dehydrogenation reaction by using the olefin products of the dehydrogenation reaction. The catalysts have been found to be compatible, and great efficiencies can be realized.

DETAILED DESCRIPTION OF THE INVENTION

The present invention provides a novel method for preparing alkyl aromatics. The method involves the dehydrogenation of an alkane to prepare the olefins, and reacting the olefins produced with an arene reactant in an aromatic alkylation reaction. The catalyst used is a dual catalyst system, providing catalysis to both reactions, which are conducted simultaneously in a single reactor.

The catalyst used in the dehydrogenation of the alkane is a dehydrogenation catalyst. Such catalysts are well known, and can include, in particular, pincer-ligated iridium complexes, both PCP and NCN types. Other soluble dehydrogenation catalysts can also be used. There are many pincer catalysts and other potential catalysts. See, e.g., van Koten et al., *J. Mol. Catal., A: Chem.* 146:317-323 (1999); The Chemistry of Pincer Compounds; Morales-Morales, D. Jensen, D. Eds.; Elsevier: Amsterdam, 2007.

In one embodiment, the dehydrogenation catalyst used is an iridium catalyst complex. Both PCP and NCN pincer-ligated iridium complexes are appropriate. In one embodiment, the dehydrogenation catalyst is $(^{iPr}PCP)IrH_4$. In one embodiment, the iridium is coordinated with a benzimidazolyl-containing ligand to form an NCN type complex.

The iridium catalyst complex can also be combined with an activating cocatalyst. The activating cocatalyst can be selected from the group consisting of alkylalumoxanes, aluminum alkyls, aluminum halides, alkyl aluminum halides, Lewis acids such as tris(pentafluorophenyl)borane, alkylating agents, hydrides such as lithium hydride, reducing agents such as Na/K amalgam, and mixtures thereof. The preferred ratio of metal complex to activating cocatalyst is from $1:10^{-2}$ to $1:10^6$.

The composition described above may also be supported. The support material may be a porous material, which includes, but is not limited to, inorganic oxides, zeolites, and inorganic chlorides. The support may also be resinous materials such as polystyrene, polyolefin, and other polymeric materials. These catalysts may be physiosorbed on the support or chemically bonded to the support.

The alkanes subjected to dehydrogenation can be any suitable alkane, straight chain or branched. In one embodiment, the alkane is an n-alkane. In another embodiment, the alkane can be a $C_6$-$C_{30}$ alkane. In another embodiment, the alkane reactant comprises a $C_{12}$ alkane or lower.

The alkane is combined with an aromatic reactant and the dual catalyst system, i.e., the dehydrogenation and alkylation catalyst, in a single reactor. The first step that occurs in the generation of olefins.

Once the olefins have been generated by dehydrogenation of the alkane, the alkylation reaction with the aromatic reactants will take place. The aromatic reactants are present in the reactor so that the reaction occurs within the same reactor as the dehydrogenation. The alkylation reaction will actually begin to occur simultaneously once the dehydrogenation reaction is started, as the olefin product from the alkylation reaction will react as formed with the aromatic reactant to generate the alkyl aromatic compound.

The aromatic reactant can be any suitable aromatic reactant, such as benzene or naphthene. The aromatic reactant is added to the reactor as a reactant so it is available as soon as the olefins are generated. Thus, the alkylation reaction occurs immediately.

The catalyst in the dual catalyst system used for the alkylation reaction is generally any suitable alkylation catalyst. Many such catalysts are known. In one embodiment, the catalyst is an acidic catalyst such as an alumina-silicate or a simple zeolite catalyst. In one embodiment, the catalyst is comprised of a $H^+SZ25$ of β-zeolite.

The consumption of the olefins in the alkylation reaction will drive the dehydrogenation reaction to completion. In another embodiment, hydrogen, which is a valuable by-product of the dehydrogenation reaction, is removed from the reactor in order to further drive the reaction to completion. The recovered hydrogen can then be passed on to storage or used in another reaction within the plant. Overall, the process is quite efficient due to the modes used to drive the reaction to completion, and due to the reaction occurring in a single reactor.

The reaction can be run under conventional dehydrogenation and alkylation reaction conditions of temperature and pressure. Solvents can be used as are appropriate. The important aspect is that the conditions are selected to best enhance all of the reactions occurring in the reactor with the chosen catalysts.

Another advantage is the preparation of an aromatic bicyclic species. The prepared alkylaromatic can also be used to prepare the bicyclic component. The dual catalyst system has been found to drive a reaction to form bicyclic species. The alkyl group is dehydrogenated, but cyclization can also occur to form the bicyclic species.

The following examples are provided to further illustrate the present invention, but are not meant to be limiting.

EXAMPLE 1

The following reaction Scheme—Scheme 1 below—was conducted using pentylbenzene as an alkylaromatic, and with a dual catalyst system comprising one of the dehydrogenation catalysts noted in Scheme 2, and with $H^+SZ25$ or β-zeolite. The results are shown in Table 1 below.

Scheme 1

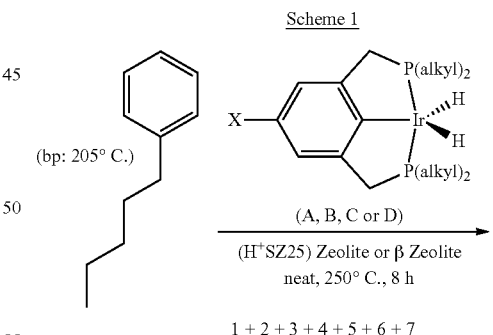

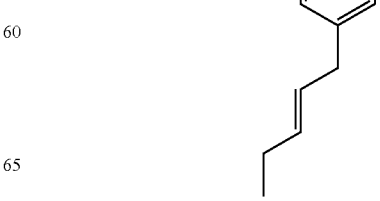

1

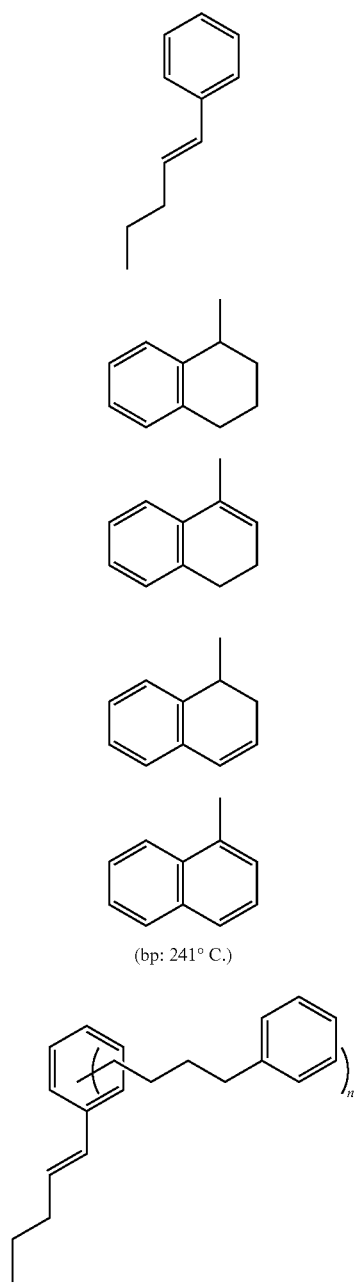

The complexes shown in Scheme 2 were investigated as dehydrogenation catalysts. H⁺SZ25 and "β-zeolite" (provided by Chevron) were used as the tandem catalysts in the dual catalyst system.

Scheme 2. Dehydrogenation catalysts

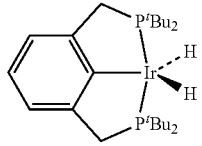

A

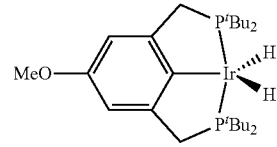

B

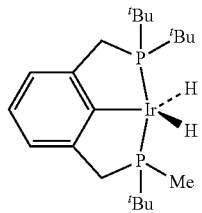

C

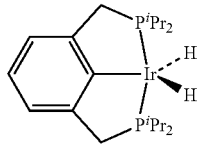

D

TABLE 1

Concentrations (mM) and conversions (% based on pentylbenzene) resulting from tandem dehydrogenation-arylation of pentylbenzene at 250° C.[a]

| run | Ir cat | zeolite | 1 | 2 | % conv. DeH2td only | 3 | 4 | 5 | 6 | % conversion to cyclics | 7 (bimolec) | % convert to bimolec | Total % conversion (calcd) |
|---|---|---|---|---|---|---|---|---|---|---|---|---|---|
| 1 | A | β | 25 | 26 | 1 | 145 | 0 | 2 | 1 | 3 | 29 | 0.5 | 4 |
| 2 | B | β | 98 | 247 | 6 | 487 | 34 | 104 | 38 | 11 | 37 | 0.6 | 18 |
| 3 | C | β | 150 | 220 | 6 | 262 | 0 | 15 | 5 | 5 | 46 | 0.8 | 12 |
| 4 | A | H⁺SZ25 | 10 | 15 | 0 | 695 | 14 | 27 | 34 | 13 | 18 | 0.3 | 14 |
| 5 | B | H⁺SZ25 | 41 | 61 | 2 | 1138 | 40 | 265 | 231 | 29 | 22 | 0.4 | 31 |
| 5' | B | H⁺SZ25 | 33 | 57 | 2 | 1165 | 42 | 186 | 163 | 27 | 23 | 0.4 | 29 |
| 6 | C | H⁺SZ25 | 19 | 44 | 1 | 1256 | 28 | 60 | 60 | 24 | 50 | 0.9 | 26 |

TABLE 1-continued

Concentrations (mM) and conversions (% based on pentylbenzene) resulting from tandem dehydrogenation-arylation of pentylbenzene at 250° C.[a]

| run | Ir cat | zeolite | 1 | 2 | % conv. DeH2td only | 3 | 4 | 5 | 6 | % conversion to cyclics | 7 (bimolec) | % convert to bimolec | Total % conversion (calcd) |
|---|---|---|---|---|---|---|---|---|---|---|---|---|---|
| 7 | D | H+SZ25 | 70 | 40 | 2 | 1343 | 100 | 92 | 75 | 28 | 0 | 0.0 | 30 |
| 7' | D | H+SZ25 | 20 | 46 | 1 | 1070 | 34 | 25 | 32 | 20 | 5 | 0.1 | 21 |
| 8 | B[b] | none | 1 | 442 | 8 | 0 | 0 | 0 | 0 | 0 | 0 | 0.0 | 8 |
| 9 | B[b] | H+SZ25 | 2 | 4 | 0 | 118 | 0 | 2 | 13 | 2 | 0 | 0.0 | 2 |
| 10 | none | H+SZ25 | 0 | 0 | 0 | 0 | 0 | 0 | 0 | 0 | 0 | 0.0 | 0 |

[a]Reactions conducted with 2.0 mM catalyst solution unless indicated otherwise; 8 h reflux (ca. 205° C.), immersed in an oil bath at 250° C.
[b]Reactions conducted with 29.0 mM catalyst solution.

As seen in Table 1, after heating for 8 hours, high turnover numbers were effected, resulting in conversions of saturated substrate as high as 31%. It is believed the cyclized product 3 derives from zeolite-catalyzed cyclization of either 1-pentenylbenzene (the presumed major kinetic dehydrogenation product) or from 2-pentenylbenzene (which would be formed by isomerization of 1-pentenylbenzene). Products 4, 5 and 6 presumably result from secondary dehydrogenation of 3.

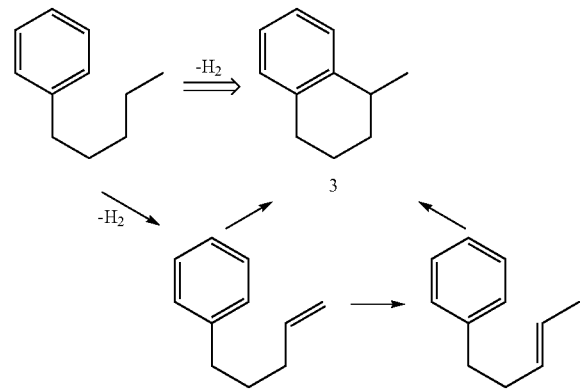

It should be noted that the results indicate synergy: in the absence of zeolite, the iridium catalyst alone does not afford conversions (to acyclic dehydrogenated product) that are nearly as high as the conversion to cyclic products obtained by the tandem or dual systems. Thus this is more than an "iridium-to-zeolite-handoff" of olefin; the zeolite component is successfully "pulling" the reaction.

This is believed a result of the olefin being consumed, and therefore not inhibiting the dehydrogenation catalysis.

Both β-zeolite and H+SZ25 are found to be effective, but total conversions are significantly greater with H+SZ25. The greater effectiveness of H+SZ25 is also reflected in the higher concentrations of noncyclized dehydrogenated product remaining when the reaction is over (see, runs 3 and 6, both using the same dehydrogenation catalyst, C).

Importantly, although the major products are cyclized, significant amounts of bimolecular products are observed. Slightly higher yields are obtained with β-zeolite than with H+SZ25. It seems plausible that this difference simply reflects the lower rate of cyclization by β-zeolite (rather than a higher rate of intermolecular reaction); this would result in higher steady-state concentration of acyclic olefin, favoring the bimolecular reaction.

EXAMPLE 2

Representative Reaction

Inside a glovebox, 2.69 mL of a 2.0 mM solution containing pentylbenzene and the catalyst (MeO-tBuPCP)IrH$^2$ was combined with a zeolite (0.577 g of the zeolite "H+SZ-25" or 25% by weight), and hexamethylbenzene as an internal standard (0.149 g, 0.918 mmol). The mixture was combined in a reactor consisting of a 5-mL round-bottom flask fused to a water jacketed condenser. The top of the condenser is connected by an O-ring adaptor with an argon inlet and outlet. The reaction was heated in an oil bath at 250° C. for 8 hours and yields were reported similar to those in Table 1.

Various modifications and alterations of this invention will become apparent to those skilled in the art without departing from the scope and spirit of the invention. Other objects and advantages will become apparent to those skilled in the art from a review of the preceding description.

A number of patent documents and non-patent documents are cited in the foregoing specification in order to describe the state of the art to which this invention pertains. The entire disclosure of each of the cited documents is incorporated by reference herein.

Furthermore, the transitional terms "comprising", "consisting essentially of" and "consisting of", when used in the appended claims, in original and amended form, serve to indicate what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All iridium catalyst complexes and methods of use thereof that embody the present invention can, in alternate embodiments, be more specifically defined by any of the transitional terms "comprising", "consisting essentially of" and "consisting of".

That which is claimed is:
1. A process for preparing alkyl aromatics, comprising:
   providing in the same reactor at least one alkane, at least one aromatic compound, and a dual catalyst system comprising:
   a dehydrogenation catalyst comprising a pincer-ligated iridium catalyst, and an alkylation catalyst comprising a zeolite selected from the group consisting of $H^+SZ25$ and a β-zeolite, wherein the dehydrogenation and alkylation reactions occur concurrently within the same reactor to prepare the alkyl aromatics.

2. The process of claim 1, wherein the pincer-ligated iridium complex is a PCP or NCN complex.

3. The process of claim 2, wherein the pincer-ligated iridium complex is a PCP complex.

4. The process of claim 3, wherein the pincer-ligated iridium complex is $(^{iPr}PCP)IrH_4$.

5. The process of claim 2, wherein the pincer-ligated iridium complex is a NCN complex.

6. The process of claim 5, wherein the iridium in the iridium catalyst is coordinated with the nitrogen atoms in a benzimidazolyl-containing ligand to form an NCN pincer ligand complex.

7. The process of claim 1, wherein the dehydrogenation catalyst further comprises a co-catalyst.

8. The process of claim 1, wherein the reaction is run in a closed system.

9. The process of claim 1, wherein the alkane is a $C_6$-$C_{30}$ alkane.

10. The process of claim 1, wherein the alkane is a $C_{12}$ alkane or lower alkane.

11. The process of claim 1, wherein the aromatic compound comprises benzene.

* * * * *